(12) United States Patent
Hanna

(10) Patent No.: US 9,566,362 B1
(45) Date of Patent: Feb. 14, 2017

(54) POURED AND/OR COMPRESSED MULTIPLE WAX OBJECT

(71) Applicant: Burton Hanna, Fayetteville, AR (US)

(72) Inventor: Burton Hanna, Fayetteville, AR (US)

( * ) Notice: Subject to any disclaimer, the term of this patent is extended or adjusted under 35 U.S.C. 154(b) by 0 days.

(21) Appl. No.: 14/161,797

(22) Filed: Jan. 23, 2014

(51) Int. Cl.
*A61L 9/02* (2006.01)
*B26F 3/00* (2006.01)

(52) U.S. Cl.
CPC ... *A61L 9/02* (2013.01); *B26F 3/00* (2013.01)

(58) Field of Classification Search
CPC ............ A61L 9/012; A61L 9/02; A61L 9/035; B26F 3/00; B65D 1/36; B65D 5/48; B65D 5/48046; B65D 5/49; B65D 21/0204; B65D 25/04; F21V 35/00; C11C 5/008
USPC ......... 206/447; 220/507, 523; 422/125, 126; 431/289–295, 288
See application file for complete search history.

(56) References Cited

U.S. PATENT DOCUMENTS

| | | | | |
|---|---|---|---|---|
| 2,083,081 A * | 6/1937 | Moll | ...................... | A23G 9/083 249/120 |
| 4,428,493 A * | 1/1984 | McDonough | ............ | B65D 1/24 206/518 |
| 4,887,790 A * | 12/1989 | Wilkinson | ................ | A61J 3/06 220/507 |
| 5,660,281 A * | 8/1997 | James | ...................... | B65D 1/36 249/120 |
| 6,609,627 B1 * | 8/2003 | Clarke | ................. | B65D 43/162 220/523 |
| 7,067,772 B2 | 6/2006 | Tanner et al. | ............... | 219/445.1 |
| 7,699,603 B2 | 4/2010 | Furner et al. | ................. | 431/292 |
| 2002/0102187 A1 * | 8/2002 | Bellenger | ............... | A61L 9/035 422/126 |
| 2006/0018786 A1 * | 1/2006 | Tolman | ................... | A61L 9/035 422/125 |
| 2007/0020571 A1 * | 1/2007 | Burkhamer | ............. | C11C 5/008 431/288 |
| 2008/0070174 A1 * | 3/2008 | Moeller | ................... | C11C 5/008 431/289 |
| 2010/0078339 A1 * | 4/2010 | Bar-Or | ..................... | C11C 5/008 431/295 |

* cited by examiner

*Primary Examiner* — Bryon Gehman
(74) *Attorney, Agent, or Firm* — Keisling & Pieper PLC; Trent C. Keisling

(57) ABSTRACT

The invention includes an improved multiple component wax object that may be advantageously cubic or in another shape such as similar to tree bark that may be melted in a conventional warmer or candle melting device. Packaging for the cubic wax melts may be advantageously employed as a layered container for cooling as well as storing and transporting a group of wax melts. Packaging for the melts may also serve as discrete containers for several melts having different constituents.

3 Claims, 9 Drawing Sheets

POURED AND/OR COMPRESSED MULTIPLE WAX OBJECT

CROSS-REFERENCE TO RELATED APPLICATIONS

This application claims priority to and is a continuation-in-part of application Ser. No. 14/099,646, filed Dec. 6, 2013.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The invention pertains to improvements in candles and more particularly to those types of candles employed with plate warmers that melt the candle wax to emit the fragrance therefrom. Known art can be found in U.S. Class 219, subclass 445.1 and in Class 219, subclass 292 and in other classes and subclasses.

2. Description of the Known Art

Those skilled in the art will appreciate that it is often desirable to dispense fragrances from candles without actually burning the candle. Devices such as candle warmers and plate warmers and the like have been developed to melt candles without using a flame, typically by an electrically powered burner that simply melts the candle. Other types of waxes without wicks and with fragrances may also be used with these systems. While conventional candles may be used with such systems, they do not work as well as smaller wax objects such as cubes or the like that are specifically made for such warmers. The wax objects are typically sized to melt completely and uniformly on the warmer and have a high concentration of fragrance per volume of the carrier (i.e. the wax). While it is known in the art to make candles with multiple components or layers of wax and/or fragrances, because of their smaller size, the combination of individual components has not been done with small wax objects for warmers.

Known art which may be relevant to the present invention includes the following patents with their abstracts, the teachings of which are incorporated by reference.

U.S. Pat. No. 7,067,772, issued to Tanner, et al., on Jun. 27, 2006, entitled Candle warming apparatus, is for a hot plate warming apparatus adapted to warm a candle or other object resting thereon, as well as to provide illumination that simulates the effects of a lighted burning candle. The apparatus may include an adjustable cord apparatus, a light source, and/or a component enabling attachment of other peripheral components. The light source is positioned proximal to the hot plate for providing illumination to an object or substance resting on the hot plate or housing. The adjustable cord apparatus provides electricity to the warming apparatus while allowing a user to alter the length of the cord that is extending from the warming apparatus. The apparatus also comprises a blower to facilitate heating of a candle placed thereon, as well as to cause scented particles emanating from the melted wax or wax-like substance to be better dispersed or dissipated into the surrounding air. The attachment component permits additional peripheral components or materials to be removably coupled to the warming apparatus, such as interchangeable face plates, covers, craft objects, or module objects.

U.S. Pat. No. 7,699,603, issued Furner, et al., on Apr. 20, 2010, entitled Multisensory candle assembly, is for a candle assembly that includes a support base with a melting plate upon which a meltable solid fuel rests and a wick holder to hold a wick and engage the meltable solid fuel, and a control unit having at least one electrical component to control at least one of a sound emitting system or a light emitting system. In another aspect, a candle assembly includes a sensor configured to detect the presence of a flame disposed on the wick and controls the at least one of the sound emitting system or the light emitting system, and a lock and key mechanism. Another candle assembly includes a replaceable container to hold a meltable fuel element with a wick and a first mating surface and a control unit having at least one electrical component to control at least one of a sound emitting system or a light emitting system. In another aspect, the control unit has a second mating surface complimentary to the first mating surface and a sensor configured to detect the presence of a flame disposed on a wick. The sensor controls the at least one of the sound emitting system or the light emitting system, and the first mating surface is configured to mate with the second mating surface in a pre-selected spatial orientation to permit the sensor to detect the presence of a flame.

Also, commercially available equipment and components may be relevant, including commercial plate warmers or candle warmers or the like. Such equipment may be used in implementing an exemplary embodiment in accordance with the present invention.

None of these references, either singly or in combination, disclose or suggest the present invention. It is desirable to have an improved encryption system method for data to address the perceived shortcomings of the known art.

While it is evident from past attempts that devices for melting candles and wax are known, candles or wax particularly adapted for melting plates and similar devices where the wax objects are relatively small and easily melted at low temperatures and with differing colors and/or fragrances have not been used but are desirable.

SUMMARY OF THE INVENTION

The present invention addresses the perceived needs in the known art discussed above. In this regard, the present invention substantially fulfills this need. The new wax objects of the present invention provide a small wax cubic that may be advantageously employed with conventional wax warmers and/or candle melting devices.

In one exemplary embodiment in accordance with the present invention an improved cubic wax object is provided that is highly fragranced but composed of multiple wax layers.

In another exemplary embodiment, the system may be used to provide irregularly shaped but thin wax objects similar to tree bark in appearance and highly fragranced that may also be advantageously employed with conventional wax warmers and/or candle melting devices.

In addition to providing the features and advantages referred to above, it is an object of the present invention to provide a data system that verifies the pickup and dropoff of materials.

It is another object of the present invention to provide a fragrance dispensing system that uses small uniform wax carriers with multiple wax components with discrete fragrances.

It is still another object of the present invention to provide an improved wax object for melting.

It is an object of the present invention to provide a data system that may be easily retrofitted and adapted to existing devices.

These and other objects and advantages of the present invention, along with features of novelty appurtenant thereto, will appear or become apparent by reviewing the following detailed description of the invention in conjunction with the appended drawings.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views:

FIG. 11 is an end plan view taken generally from the front of FIG. 10;

DETAILED DESCRIPTION OF THE INVENTION

The present invention addresses the perceived needs in the known art discussed above. In this regard, the present invention substantially fulfills this need.

In one exemplary embodiment, a multi-colored cube of wax used for the purpose of home fragrance as best seen in FIGS. 1-4. The cubes 20 are used by melting in a simmering pot to disperse the fragrance encapsulated in the wax. The reason of this is so that the manufacturer can mix and match different fragrances within the cube itself. For instance a hazelnut and vanilla could be combined to create a toffee smell, or any other combination of color and fragrance. The colors run horizontally (FIGS. 2-4), and can be made in 2 or 3 different colors and scents per cube.

Figure 1:
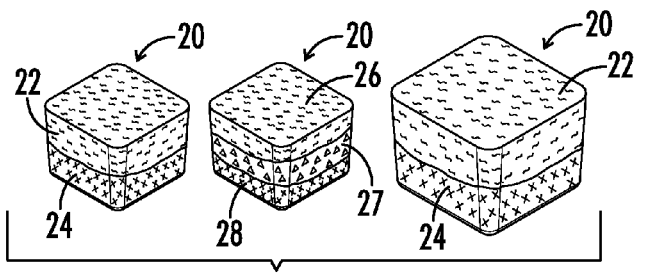
FIG. 1 is a perspective view showing several wax melts in accordance with one exemplary embodiment of the Poured and/or Pressed Multiple Component Wax Object in accordance with the present invention.
Figure 2:
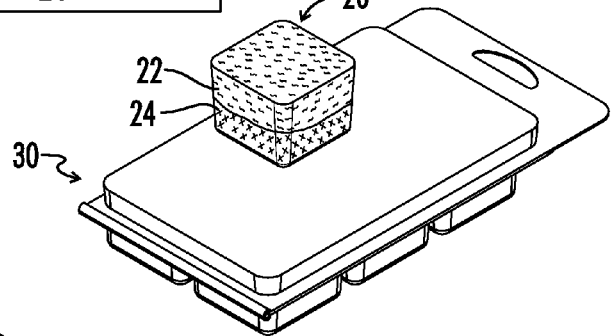
FIG. 2 is a perspective view showing a double wax melt on a 2×3 package and showing another exemplary embodiment thereof.
Figure 3:
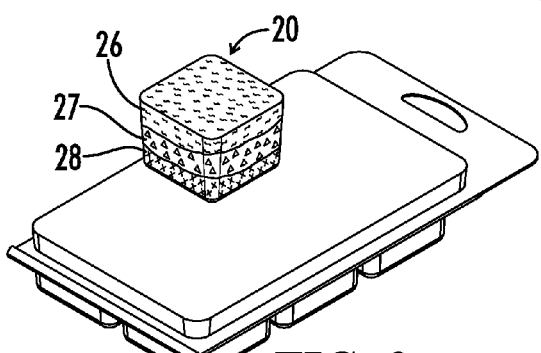
FIG. 3 is a perspective view showing a triple wax melt on a 2×3 package and showing another exemplary embodiment thereof.
Figure 4:
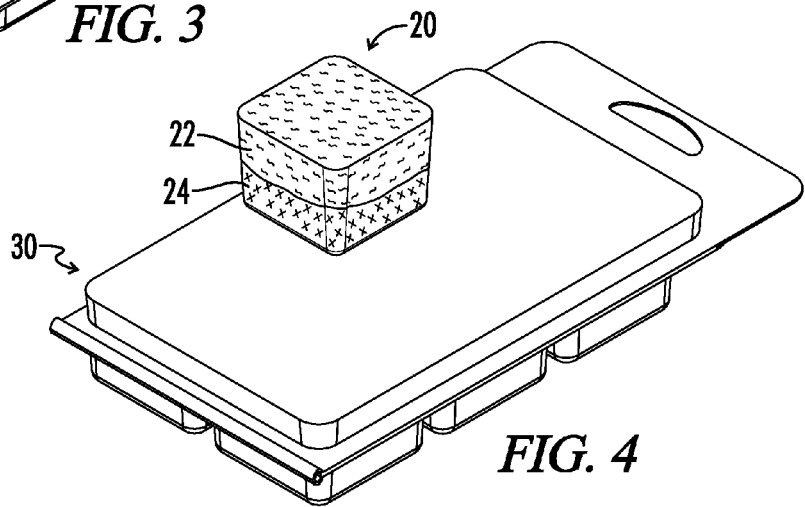
FIG. 4 is a perspective view showing a larger double wax melt on a 2×3 package and similar to FIG. 2 and showing another exemplary embodiment thereof.

In FIGS. 2 and 4, the wax cube 20 is a double pour having a top layer 22 and a bottom layer 24 while in FIG. 3 the wax cube 20 is a triple pour having a top layer 26, a middle layer 27 and a bottom layer 28. The wax cubes 20 may be sold in a clam-shell package 30 or other suitable packing. An advantage of the clam-shell package 30 is that the wax melts can be poured directly into the package, which can be a plastic 2×3 package meaning it is 2 cubes across and 3 cubes wide.

The method of manufacture is either by pressing powdered wax on a rotary powder (tablet) press or by pouring scented and colored molten wax in a thermoformed plastic tray. Different colors are achieved by pouring one layer of scented and colored wax and letting the wax cool to below its melt point before pouring the next colored layer of wax, and repeating this until you get the desired number of colored/fragranced layers. Pouring the thermoformed plastic trays can be done on a static table or on an automatic candle filling line.

The powdered wax cubes are pressed either on a horizontal opposing ram press like a Weissbach candle press, or on a rotary tablet press like a Stokes. The different colors on the rotary press are achieved by introducing different colors by adjusting the cams of the table press to lower the bottom die before passing thru another powder filling station, until getting the correct layers of colored and scented wax into the barrel section of the die before compacting the cube with the top and bottom punch.

Figure 5:
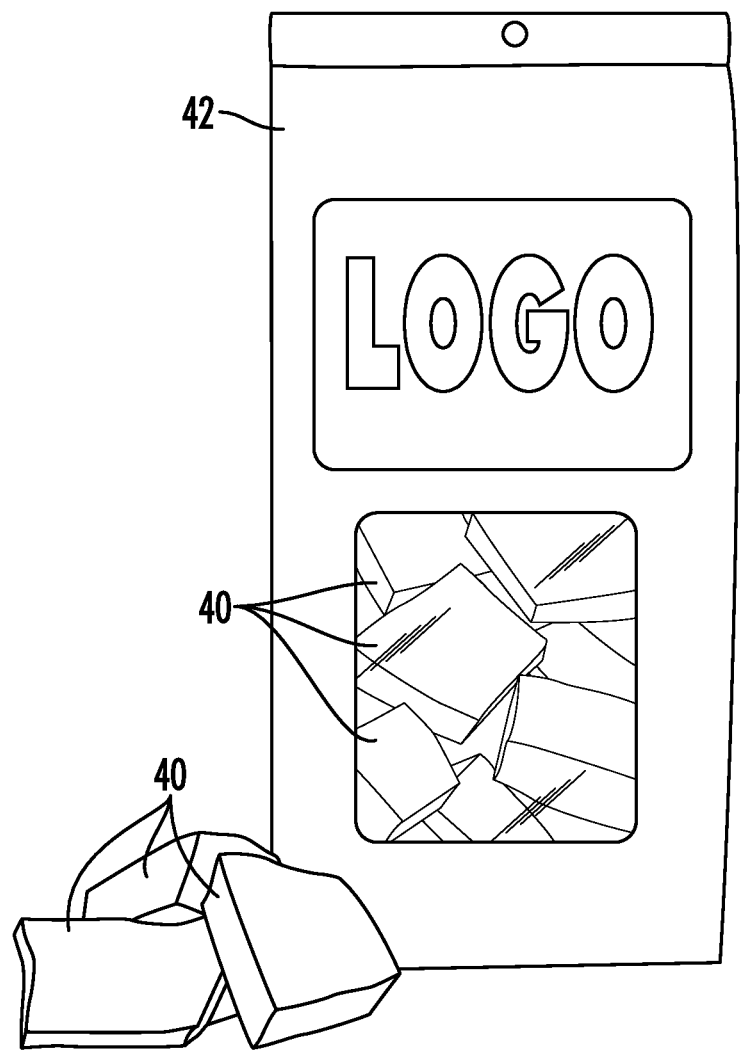
FIG. 5 is a perspective view showing a bark type wax melts adjacent a package and showing another exemplary embodiment thereof.
Figure 6A:
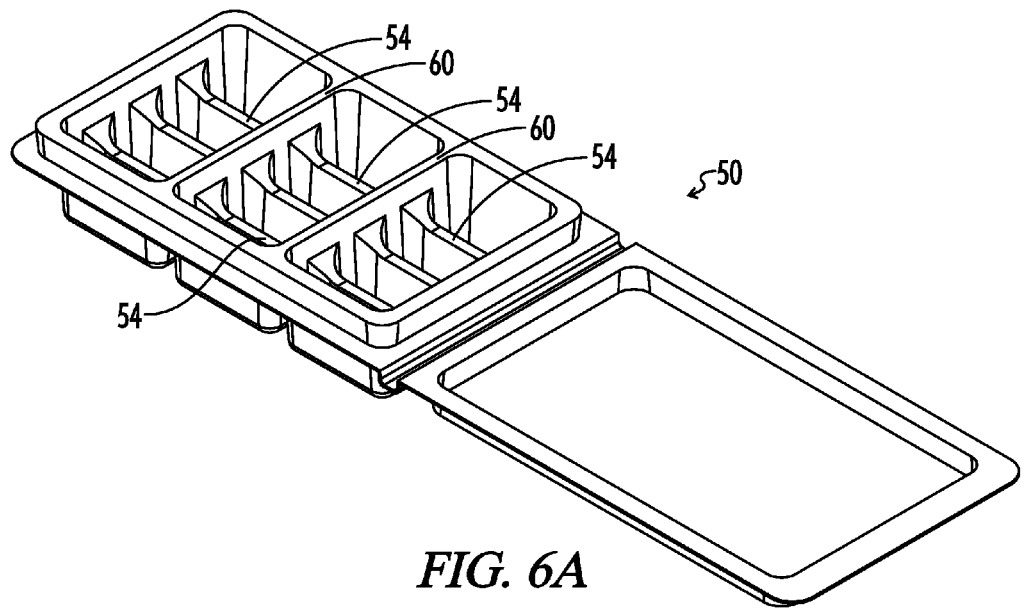
FIG. 6A is a perspective view showing an empty 3×4 package with an open lid and showing wax melts therein and showing another exemplary embodiment thereof.
Figure 6B:
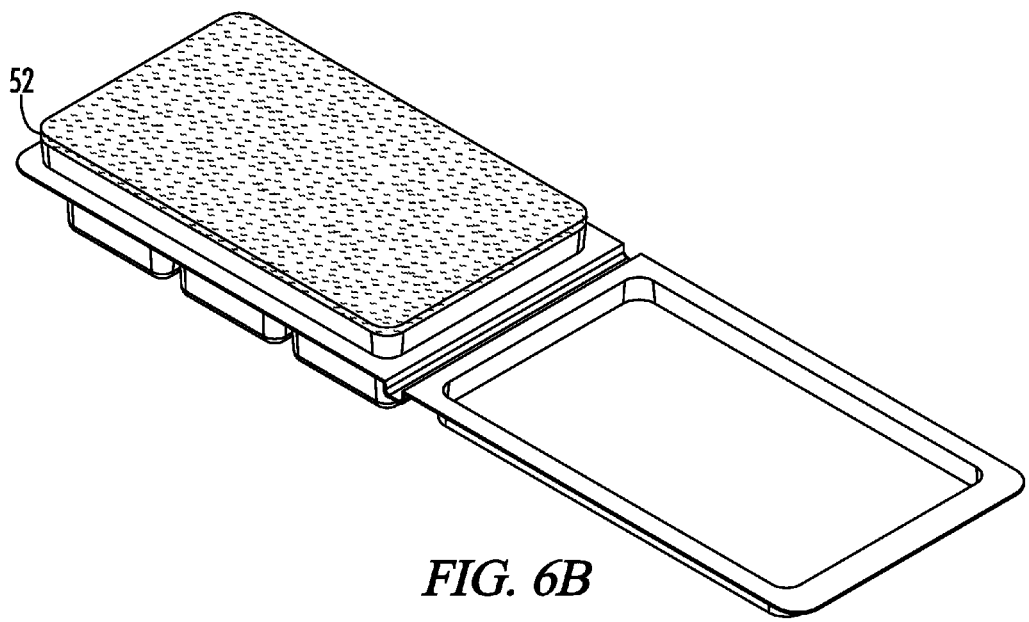
FIG. 6B is a perspective view showing a 3×4 package with an open lid and showing wax melts therein and showing another exemplary embodiment thereof.
Figure 7:
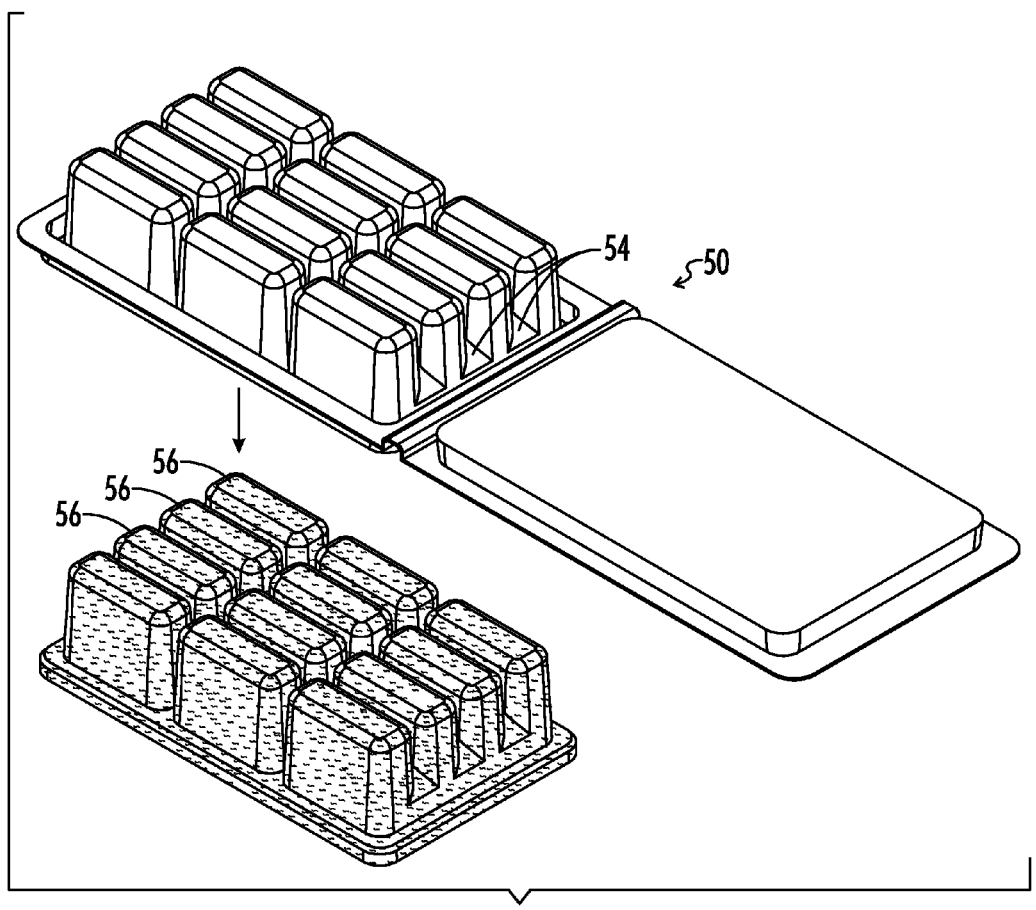
FIG. 7 is a perspective view showing the packaging and with a wax melt removed from a 3×4 package with an open lid.
Figure 8:
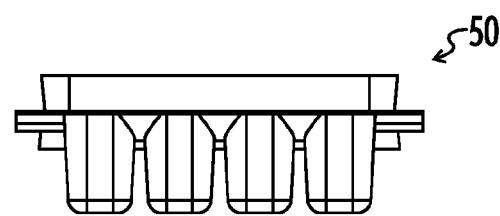
FIG. 8 is a side elevational view taken generally from the front side thereof.
Figure 9:
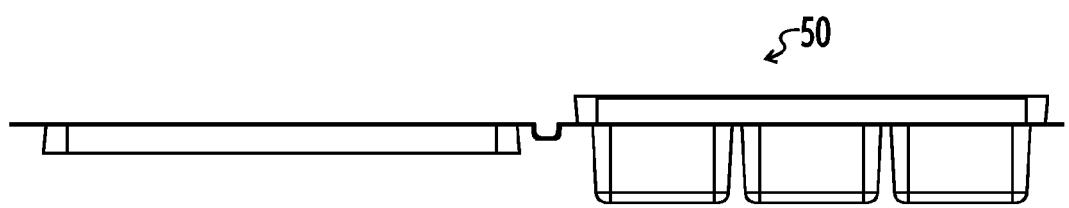
FIG. 9 is a side elevational view with the top open and with the opposite side being a mirror image thereof.
Figure 10:
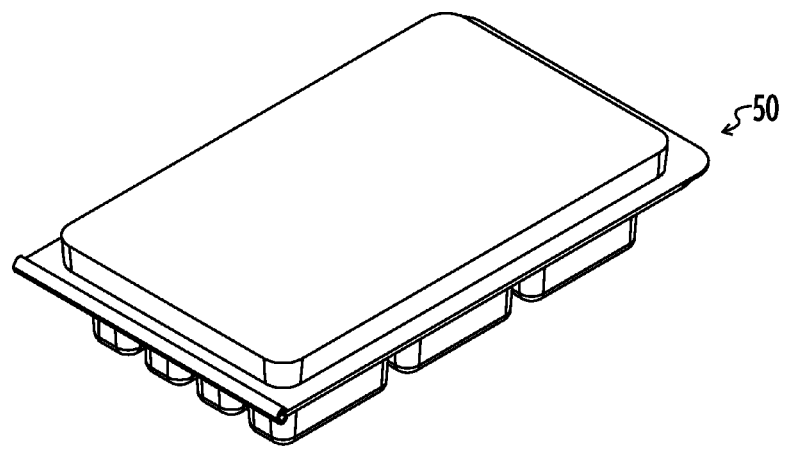
FIG. 10 is a perspective view showing a 3×4 wax melt package with a closed lid.
Figure 11:
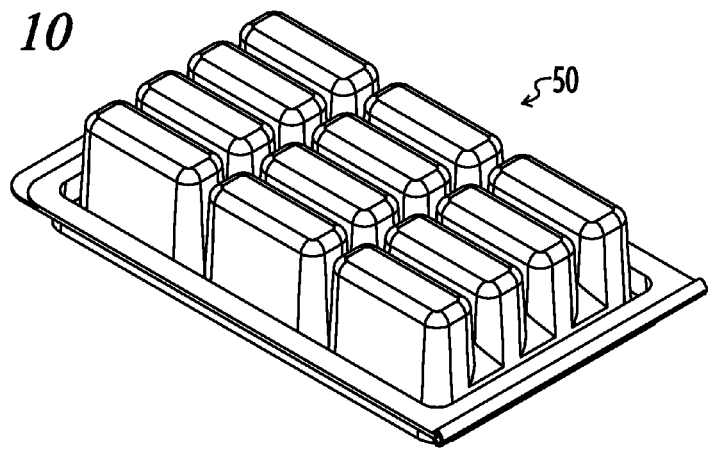
FIG. 11 is a perspective view taken generally from the bottom thereof
Figure 12:
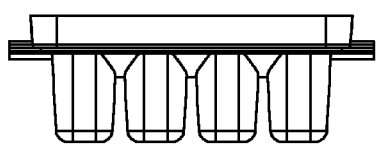
FIG. 12 is an elevational view taken generally from the rear.
Figure 13:
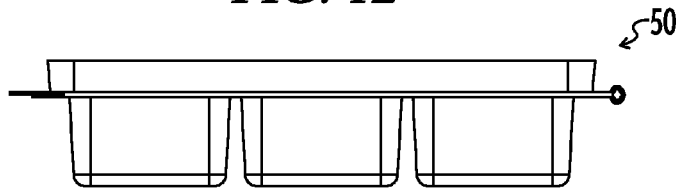
FIG. 13 is a side elevational view taken generally from the left side thereof with the opposite side being a mirror image thereof.
Figure 14:
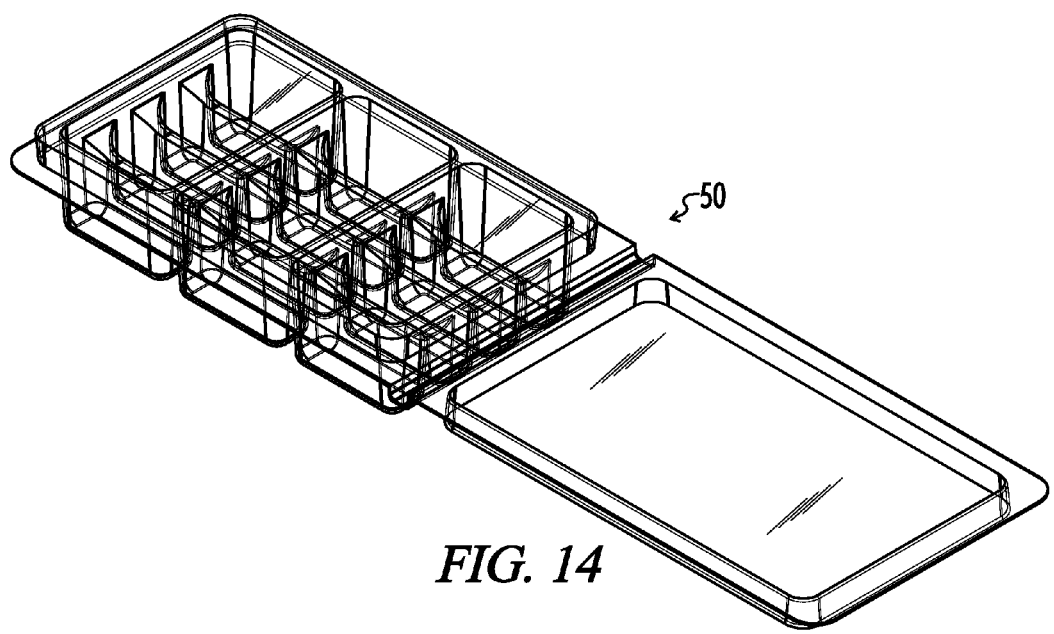
FIG. 14 is a perspective view of a clear package similar to FIG. 6A.

In another exemplary embodiment best shown in FIG. 5, irregularly shaped pieces of wax 40 similar to tree bark are provided. These pieces of wax 40 may be multi-colored and/or multi-fragranced with different colors and odor combinations. These pieces may be made by pouring molten wax into a large cooling pan to a depth of 1-3 inches. After the wax cools, the large solidified wax sheet is broken into many smaller pieces 40. The breaking can be accomplished normally (with a mallet or a hammer) or with a machine, as desired. The resultant irregularly shaped pieces 40 may then be used as wax melts or the like. They can be easily packaged in a plastic bag 42 or the like that is sealed to preserve the fragrance in the melt.

In yet another exemplary embodiment best seen in FIGS. 6-14, the clam-shell plastic packaging 50 is preferentially a 3×4 package which means it holds 3 cubes across and 4 cubes in width. Packaging for the cubic wax melts may be advantageously employed as a layered container for cooling as well as storing and transporting a group of wax melts. Most preferably, the wax is poured directly into the container 50 while a liquid with multiple layers as described hereinabove. The last layer 52 preferably covers the lateral package ribs 54 and transverse ribs 60 separating individual melts to thereby unite the individual melts 56 to enable their removal from the package as a group when desired. In use, the individual melts may be removed from the group and used singly or in combinations as described hereinabove.

Figure 15:
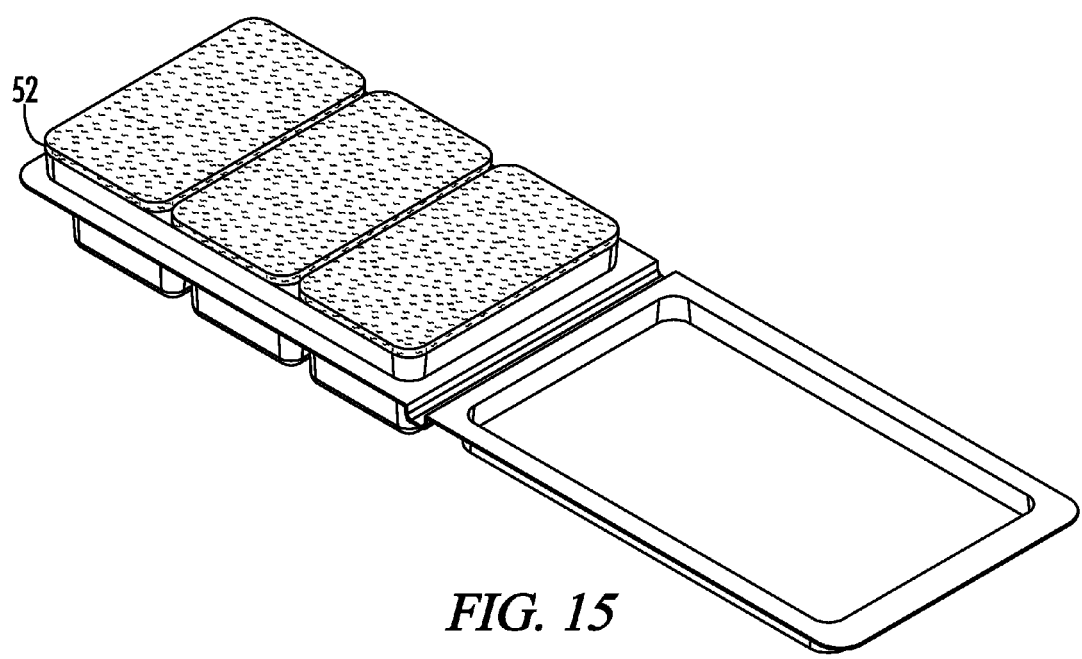
FIG. 15 is a perspective view showing a 3×4 package with an open lid and showing wax melts therein and showing another exemplary embodiment thereof; and, FIG. 16 is a perspective view showing the packaging and with a wax melt removed from a 3×4 package with an open lid.
Figure 16:
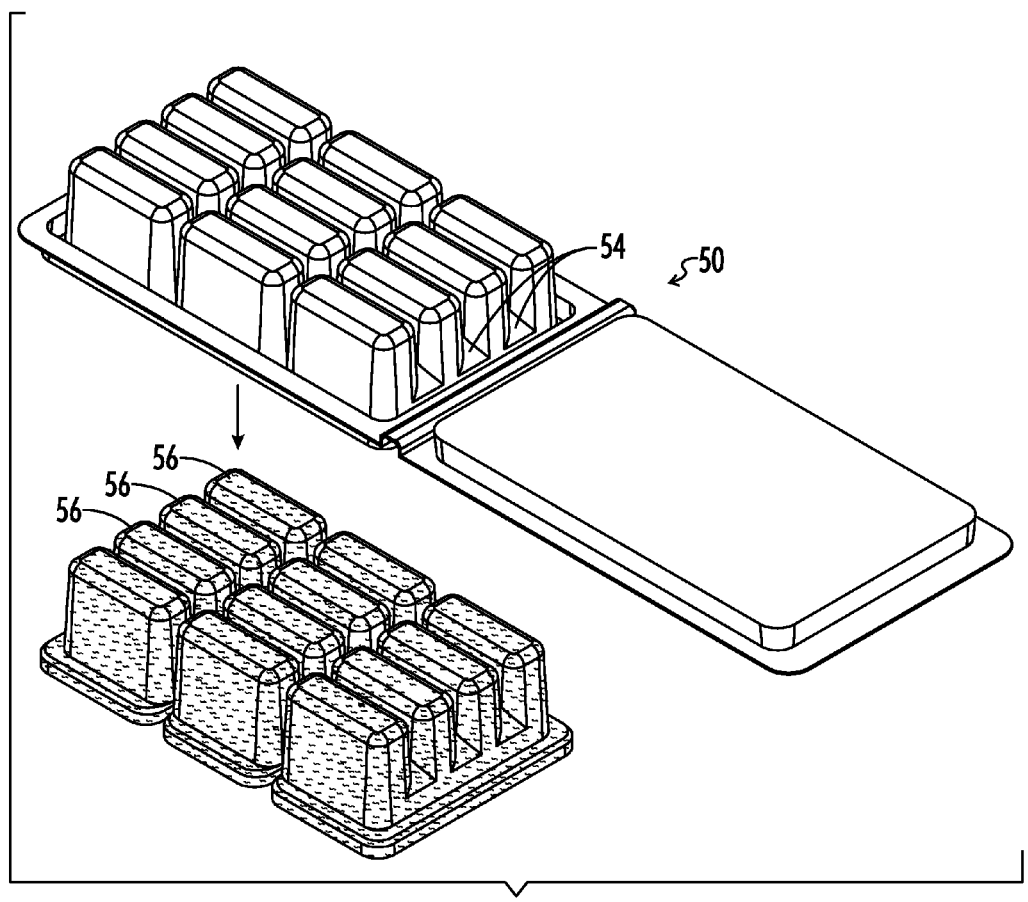

In yet another exemplary embodiment best seen in FIGS. 15-16, the clam shell packaging 50 is preferentially a 3×4 package which means it holds 3 cubes across and 4 cubes in width. Packaging for the cubic wax melts may be advantageously employed as a layered container for cooling as well as storing and transporting a group of wax melts. Most preferably, the wax is poured directly into the container 50 (which could be layered as discussed previously) and it is preferably poured into individual rows of 4 melts. Thus, a 3×4 packaging 50 would contain 3 rows of 4 melts and with each row of 4 melts being poured individually. In this manner, a first row of 4 interconnected melts could be poured and then a second row of 4 interconnected melts and then a third row of interconnected melts. In this configuration, a first fragrance (or color or other desirable component) can be placed in the first row while a second fragrance (or other component) can be placed in the second row and a third fragrance in the third row. Thus, the user has multiple melts of varying components that may be separated from the other melts and combined with for example another desirable fragrance to produce a unique fragrance.

In describing a preferred embodiment of the invention illustrated in the drawings, specific terminology has been used for the sake of clarity. However, the invention is not intended to be limited to the specific terms selected, and it is to be understood that each specific term includes all technical equivalents which operate in a similar manner to accomplish a similar purpose.

What is claimed is:

1. A package housing multiple wax melts comprising:
a bottom half with an upper peripheral lip and several cavities depending therefrom, each of the cavities receiving a melt comprising a scented wax and wherein the top of each of the cavities is below the peripheral lip such that a final pour of wax across the top of the melts creates an integral connection at the top of the cavities, resulting in a larger block of wax melt which is able to be utilized intact or broken into smaller portions; and
an upper lid adapted to fit into the peripheral lip in a closed configuration and to open upwardly into an open configuration to enable a user to access and remove a melt from the package.

2. The package of claim 1 wherein each of the cavities contains a wax melt with a different scent, thereby allowing for multiple scented wax melts to exist in the same package.

3. The package of claim 1 wherein the final pour of wax comprises multiple different scents of wax are layered on top of the cavities and culminating with a final layer of wax poured across the top of the cavities, to create a single unified block of multi-scented wax.

* * * * *